United States Patent [19]
Black et al.

[11] Patent Number: 5,676,700
[45] Date of Patent: Oct. 14, 1997

[54] INTERLOCKING STRUCTURAL ELEMENTS AND METHOD FOR BONE REPAIR, AUGMENTATION AND REPLACEMENT

[75] Inventors: Jonathan Black, King of Prussia, Pa.; Michael T. Manley, Franklin Lakes; Paul Serekian, Mahwah, both of N.J.

[73] Assignee: Osteonics Corp., Allendale, N.J.

[21] Appl. No.: 595,932

[22] Filed: Feb. 6, 1996

Related U.S. Application Data

[63] Continuation of Ser. No. 328,924, Oct. 25, 1994, abandoned.

[51] Int. Cl.$^6$ ........................................................ A61F 2/28
[52] U.S. Cl. ................................................................ 623/16
[58] Field of Search ....................................... 623/11, 16, 66

[56] References Cited

U.S. PATENT DOCUMENTS

| | | |
|---|---|---|
| 3,979,779 | 9/1976 | Zeibig et al. . |
| 4,612,053 | 9/1986 | Brown et al. . |
| 4,713,076 | 12/1987 | Draenart ............................ 623/16 |
| 4,787,906 | 11/1988 | Haris . |
| 4,808,184 | 2/1989 | Tepic . |
| 4,828,563 | 5/1989 | Muller-Lierheim . |
| 4,834,757 | 5/1989 | Brantigan . |
| 4,846,838 | 7/1989 | Takai et al. . |
| 4,880,610 | 11/1989 | Constantz . |
| 4,960,426 | 10/1990 | Atsumi . |
| 5,015,256 | 5/1991 | Bruce et al. . |
| 5,047,031 | 9/1991 | Constantz . |
| 5,067,965 | 11/1991 | Ersek et al. . |
| 5,141,510 | 8/1992 | Takagi . |
| 5,147,402 | 9/1992 | Bohler et al. . |
| 5,178,201 | 1/1993 | Ahlers ................................ 164/34 |
| 5,211,664 | 5/1993 | Tepic et al. . |
| 5,258,028 | 11/1993 | Ersek et al. ........................ 623/11 |
| 5,282,861 | 2/1994 | Kaplan . |
| 5,336,263 | 8/1994 | Ersek et al. ........................ 623/11 |
| 5,433,750 | 7/1995 | Gradinger et al. . |
| 5,571,182 | 11/1996 | Ersek et al. . |

FOREIGN PATENT DOCUMENTS

| | | | |
|---|---|---|---|
| 171546 | 9/1984 | Japan | 623/16 |

OTHER PUBLICATIONS

Anatomic Porous Replacement Hip Arthroplasty: First 100 Consecutive Cases, Lawrence D. Dorr et al, Seminars in Arthroplasty, vol. 1, No. 1, Jul., 1990, pp. 77–86.

Current Approaches to Experimental Bone Grafting, Joseph M. Lane et al, Orthopedic Clinics of North America, vol. 18, No.2, Apr. 1987, pp. 213–225.

Direct Calculation of The Surface-To-Volume Ratio for Human Cancellous Bone, D.P. Fyhrie et al, vol. 26, No. 8, pp. 955–967, 1993.

*Primary Examiner*—Michael J. Milano
*Attorney, Agent, or Firm*—Arthur Jacob

[57] ABSTRACT

Structural elements of biocompatible material are interlocked with one another in an array to repair, augment or replace natural bone, the structural elements each including a hub having a center, and a plurality of posts projecting from the hub and spaced from one another to establish inter-post spaces between adjacent posts, each post having a root at the hub, an opposite tip, a length, and a transverse cross-sectional configuration, the number of posts and the relative length, cross-sectional configuration, and location of adjacent posts in each structural element being such that the inter-post spaces of one structural element will receive the posts of adjacent structural elements in the array to promote interlocking of adjacent structural elements in a relatively tightly meshed relationship for resisting shear stress in essentially all directions within the array.

31 Claims, 3 Drawing Sheets

INTERLOCKING STRUCTURAL ELEMENTS AND METHOD FOR BONE REPAIR, AUGMENTATION AND REPLACEMENT

This application is a continuation of application Ser. No. 08/328,924, filed Oct. 25, 1994 now abandoned.

The present invention relates generally to the repair, augmentation and replacement of natural bone in the treatment of injury, disease or degeneration affecting the bone and pertains, more specifically, to a method for repairing, augmenting or replacing natural bone and to structural elements having a construction for promoting the formation of an array of structural elements, which array establishes a mechanically effective osteoconductive or osteoinductive matrix for augmenting or replacing natural bone.

Bone is among the most frequently transplanted tissue in humans. An increasing number of bone graft and bone implant procedures have been developed and performed over the years. While fresh autologous bone generally is the most effective graft material available for the repair of bone defects arising out of injury, disease or degeneration, autologous bone presents certain disadvantages, among which are limited supply, risk of further complications at the donor site, and a limited ability to create a desired functional shape for optimal repair. As a result, suitable alternatives to autologous bone are being sought.

The present invention provides an alternative to autologous bone for use in the repair, replacement or supplement of natural bone in the treatment of bone defects. In short, the present invention provides structural elements constructed of a biocompatible material and having a size and configuration enabling the elements to interlock in an array which establishes a structural matrix for attaining desirable mechanical properties while providing an osteoconductive or osteoinductive matrix for the ingrowth of natural bone. As such, the structural elements may be combined with morselized bone for use as a bone graft extender in load-bearing, as well as in non-load-bearing, applications, may be mixed with autologous blood to provide a bone graft replacement in low or non-load-bearing applications, or may be utilized alone to fill an unwanted void in the repair or replacement of natural bone. In any of the above applications, the interlocking elements of the present invention attain several objects and advantages, some of which are summarized as follows: Provides an autologous bone alternative for bone graft needs which is easily maintained on hand for ready use in a wide variety of applications; enables relatively simple and economical manufacture, utilizing currently available biocompatible materials, for ready widespread use; conserves the use of autologous bone; enables successful application in a wider variety of conditions encountered in the treatment of bone defects arising out of injury, disease or degeneration; provides ease of storage, distribution, handling and use; provides a bone graft extender having sound mechanical cohesion characteristics for load-bearing, as well as non-load-bearing, applications; provides a self-retaining bone graft replacement for low or non-load-bearing applications; provides desirable fluid characteristics for promoting filling of voids and for appropriate interfacing with surrounding bone or implants; enables economical manufacture in relatively large quantities of consistent high quality.

The above objects and advantages, as well as further objects and advantages, are attained by the present invention which may be described briefly as a structural element and an array of such structural elements interlocked with one another to augment or replace natural bone, the structural element comprising: a hub having a center; and a plurality of posts projecting from the hub and spaced from one another to establish inter-post spaces between adjacent posts, each post having a root at the hub, an opposite tip, a length, and a transverse cross-sectional configuration; the number of posts and the relative length, cross-sectional configuration, and location of adjacent posts in the structural element being such that the inter-post spaces of one structural element will receive the posts of adjacent structural elements in the array to promote interlocking of adjacent structural elements in a relatively tightly meshed relationship for resisting shear stress in essentially all directions within the array. In addition, the invention includes the method of repairing, augmenting or replacing natural bone by establishing the above array of structural elements in a void in the natural bone.

The invention will be understood more fully, while still further objects and advantages will become apparent, in the following detailed description of preferred embodiments of the invention illustrated in the accompanying drawing, in which.

Figure 1:
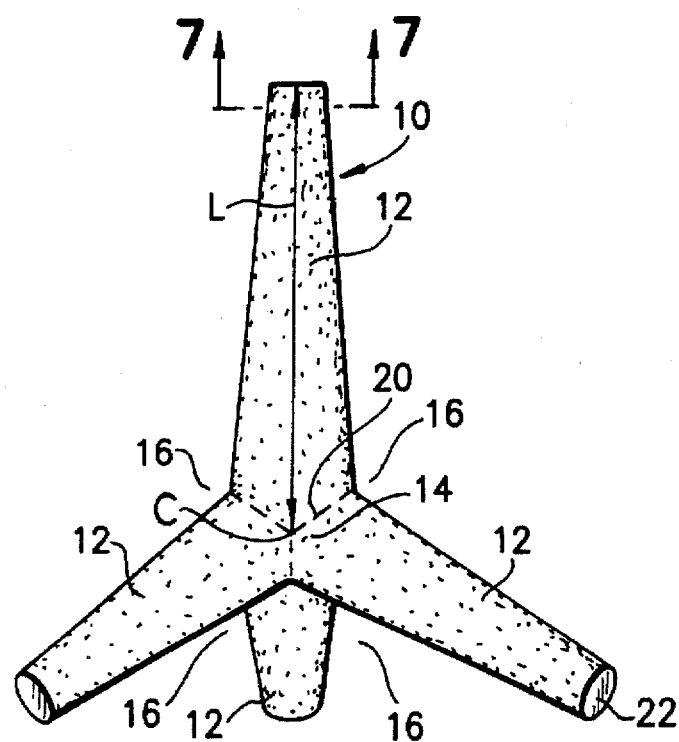
FIG. 1 is an elevational view of a structural element constructed in accordance with the present invention.
Figure 2:
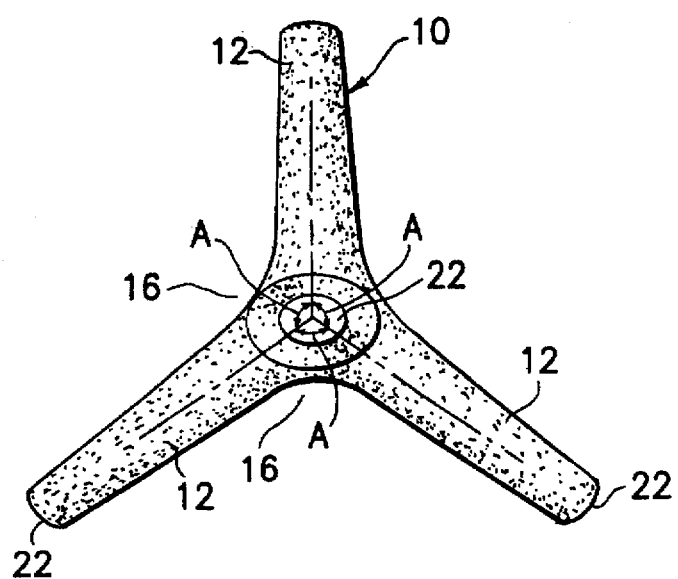
FIG. 2 is a plan view of the structural element.

Referring now to the drawing, and especially to FIGS. 1 and 2 thereof, a structural element constructed in accordance with the present invention is illustrated generally at 10 and is seen to include a plurality of posts 12 projecting from a central hub 14. Posts 12 are spaced from one another to establish inter-post spaces 16 among the posts 12, each post 12 including a root 20 at the hub 14, a tip 22 opposite the root 20, and a length L extending longitudinally along the post 12 between the center C of the hub 14 and the tip 22. In the illustrated preferred embodiment, structural element 10 has four posts 12 spaced from one another at equal angles A so that the overall configuration of the structural element 10 resembles that of a caltrop. Preferably, the posts 12 have an oval transverse cross-sectional configuration extending laterally across each post 12, as best seen in FIG. 2, wherein the posts 12 are seen to have an oval surface contour transverse to the longitudinal direction of length L, and in FIG. 7, wherein the oval surface contour of a post 12 is illustrated as an oval transverse cross-sectional configuration extending laterally across the post 12, and each post 12 is tapered from a larger cross-sectional area at the root 20 to a smaller cross-sectional area at the tip 22, all for purposes which will be described in further detail below.

Figure 3:
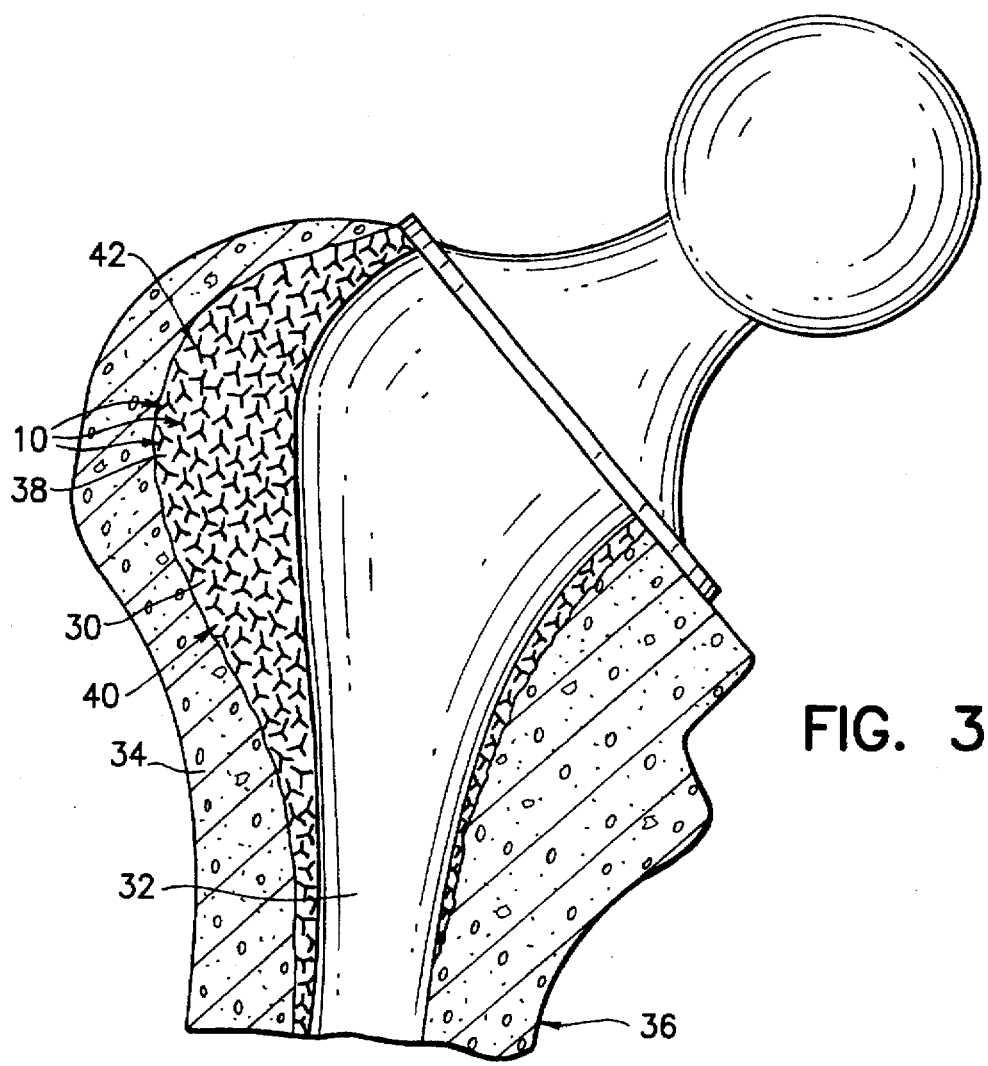
FIG. 3 is a fragmentary cross-sectional view showing a prosthetic implant in place in natural bone, with structural elements of the invention in place as a bone graft extender.
Figure 4:
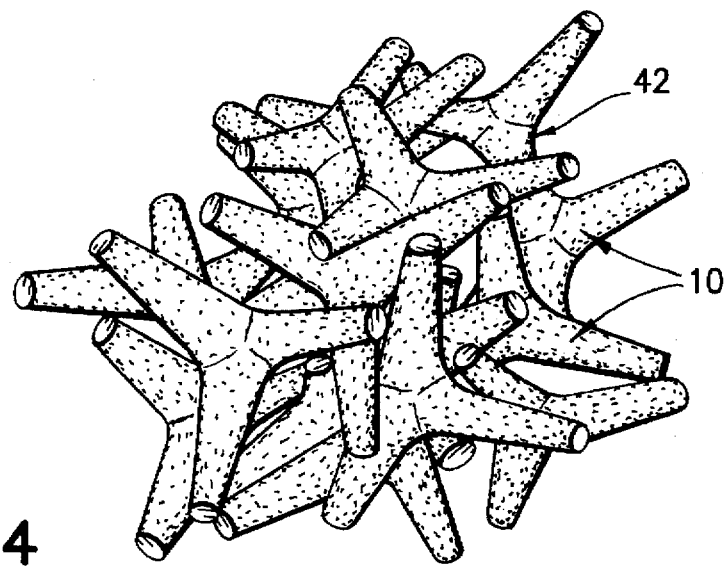
FIG. 4 is a pictorial perspective view of an array of structural elements constructed in accordance with the present invention.

In FIG. 3, structural elements 10 are shown employed as a bone graft extender in filling a void in the form of a cavity 30 between a prosthetic implant shown in the form of a femoral implant 32 and the natural bone 34 of a femur 36 which has been prepared for the reception of the femoral implant 32 in a now well-known manner. Cavity 30 is a defect resulting from a local bone loss which is a consequence of, for example, trauma, a congenital defect, local lytic process or surgical excision. The structural elements 10 have been combined with morselized bone 38 to form a mixture 40 which is received within the cavity 30 to fill the cavity 30. Mixture 40 has sufficient fluid characteristics to fill any voids within the cavity 30 and to interface appropriately with the femoral implant 32 and with the bone 34 of femur 36. The overall configuration of the structural elements 10 which overall configuration resembles that of a caltrop, enables engagement of the posts 12 with the inter-post spaces 16 in an array 42 to promote interlocking of adjacent structural elements 10 in a relatively tightly intermeshed relationship, as shown in FIG. 4 wherein only the array 42 itself is illustrated, without the surrounding morselized bone.

The tightly meshed array 42 of interlocked structural elements 10 establishes a structural matrix of sound mechanical cohesive characteristics for attaining desirable mechanical properties, while providing an osteoconductive or osteoinductive matrix for the ingrowth of natural bone. Thus, the interengaged structural elements 10 are meshed tightly enough and are interlocked to provide a structural matrix which tends to resist shear stress in essentially all directions within the array 42, while the nature of the material of the structural elements 10 allows for the ingrowth of natural bone. The oval cross-sectional configuration of the posts 12, and the tapering of the posts 12 along the length L thereof, enhance the ability of the posts 12 to enter the inter-post spaces 16 and attain meshing and interlocking of the structural elements 10 in the desired tight relationship. The mechanical strength of the matrix thus provided by the array 42 is sufficient to enable load-bearing, even upon initial implant of the femoral implant 32, whether utilized alone to fill a void such as cavity 30, or in combination with autologous bone or autologous blood.

Figure 5:
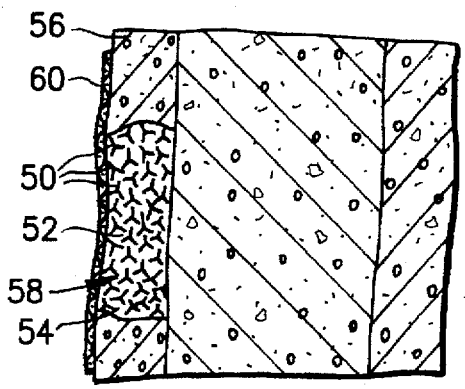
FIG. 5 is a fragmentary cross-sectional view showing a natural bone with further structural elements of the invention in place in repairing a defect in the bone.

In FIG. 5, alternate structural elements 50 are shown mixed with autologous blood 52 and employed as a bone graft replacement for filing a void in the repair of an open bone defect 54 in a bone 56. Here again, an array 58 of structural elements 50 in a tightly meshed and interlocked relationship establishes a matrix having desired mechanical characteristics as well as osteoconductive or osteoinductive characteristics. While the configuration of each structural element 50 is similar to the above-described structural element 10, structural elements 50 are relatively small in comparison to structural elements 10. The mixture of structural elements 50 and autologous blood 52 is somewhat more fluid than the mixture of structural elements 10 and morselized bone 38, and therefore is essentially non-load-bearing; however, the tightly meshed array 58 of interlocked structural elements 50 provides a matrix of sufficient mechanical strength to enable the mixture to resist shear stress adequately. An outer wrap 60 of surgical mesh assists in maintaining the shaped volume necessary for effecting the repair of open bone defect 54.

Figure 6:
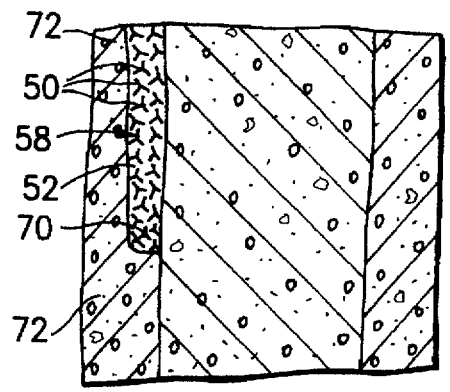
FIG. 6 is a fragmentary cross-sectional view similar to FIG. 5, but showing the repair of another bone defect.

In FIG. 6, structural elements 50 are shown mixed with autologous blood 52 and utilized as a bone graft replacement in the repair of a closed bone defect 70. Bone defect 70 is closed by virtue of being bounded by cortical bone 72, and the mixture of structural elements 50 and autologous blood 52 requires no supplemental support, such as the outer wrap 60 illustrated in FIG. 5.

For the application illustrated in FIG. 3, wherein the structural elements 10 are combined with morselized natural bone 38 as a bone graft extender, the preferred length L for the posts 12 is in the range of about 0.8 to 4.0 millimeters. Angle A is the same between all adjacent posts 12 of a structural element 10, and is equal to 109.4712°. For the applications illustrated in FIGS. 5 and 6, wherein the structural elements 50 are combined with autologous blood 52 as a bone graft replacement, the preferred length L for the posts of structural element 50 is in the range of about 80 to 400 microns. Angle A again is the same between all adjacent posts of a structural element 50, and is equal to 109.4712°.

Figure 7:
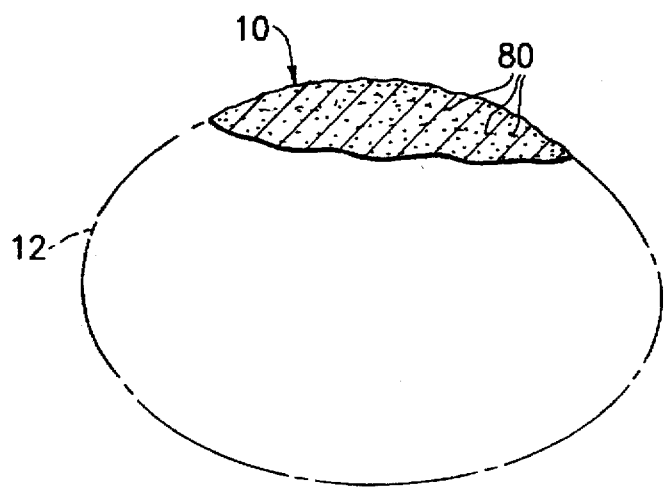
FIG. 7 is an enlarged, fragmentary cross-sectional view of a portion of the structural element taken along line 7—7 of FIG. 1 with the full transverse cross-sectional configuration of the portion of the structural element shown in phantom.
Figure 8:
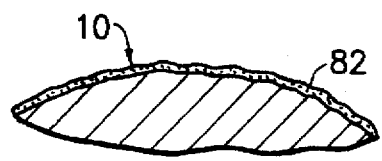
FIG. 8 is an enlarged, fragmentary cross-sectional view similar to FIG. 7, but showing an alternate embodiment.
Figure 9:
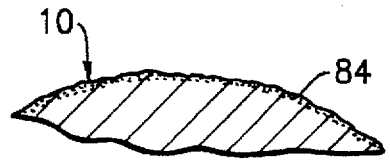
FIG. 9 is an enlarged, fragmentary cross-sectional view similar to FIG. 7, but showing another embodiment.

Structural elements 10 and 50 are best constructed of a microporous biocompatible material, a preferred currently available material being a biocompatible ceramic such as hydroxyapatite, titanium dioxide, bioactive glass and bioactive glass ceramics. The four-post caltrop-resembling configuration, as well as the dimensions, shape and relative location of the posts of the structural elements, wherein no more than two of the directions of the posts lie in a common plane, assures interengagement, meshing and interlocking of the structural elements with one another in a tightly meshed array which establishes the mechanical characteristics described above, as well as enabling interlocking with adjacent cancellous bone in filling a void contiguous with cancellous bone. In addition, the microporous nature of the preferred selected material of the structural elements, together with the relatively large internal surface area provided by the microporous characteristics of the material, enables the structural elements to carry a selected agent, such as an antibiotic or a growth factor, for dispersion at the site where the structural elements are utilized. Thus, as seen in FIG. 7, a selected agent 80 is carried within the microporous structure of the material of a structural element 10. Alternately, where the material selected for a structural element is not necessarily provided with a microporous structure, a selected agent may be coated upon the exterior surface of the structural element, as illustrated by coating 82 in FIG. 8, for dispersion at the site where the structural elements are utilized. As another alternative, a selected agent may be carried in the form of a diffused coating along the structural element, such as shown at 84 in FIG. 9. Further, the relative dimensions of the hub and the posts of structural element 50 are such that the ratio of surface area to space volume of the array of interlocked structural elements 50 is within the range of the surface-to-volume ratios encountered in human natural cancellous bone.

It will be seen that the above-described preferred embodiments of the invention attain the objects and advantages summarized above, namely: Provides an autologous bone alternative for bone graft needs which is easily maintained on hand for ready use in a wide variety of applications; enables relatively simple and economical manufacture, utilizing currently available biocompatible materials, for ready widespread use; conserves the use of autologous bone; enables successful application in a wider variety of conditions encountered in the treatment of bone defects arising out of injury, disease or degeneration; provides ease of storage, distribution, handling and use; provides a bone graft extender having sound mechanical cohesion characteristics for load-bearing applications; provides a self-retaining bone graft replacement for non-load-bearing applications; provides desirable fluid characteristics for promoting filling of voids and for appropriate interfacing with surrounding bone or implants; enables economical manufacture in relatively large quantities of consistent high quality.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A structural element for use in an array of such structural elements interlocked with one another to augment or replace natural bone, the structural element comprising:
    a hub having a center; and
    at least four posts projecting from the hub in directions relative to one another such that no more than two of the directions of any posts of the structural element lie in a common plane and the posts are spaced from one another to establish inter-post spaces between adjacent posts, each post having a root at the hub, an opposite tip, a length, and a transverse cross-sectional configuration;
    the relative length, cross-sectional configuration, and relative location of the posts in the structural element being such that upon placement of the structural elements in the array the inter-post spaces of one structural element will receive the posts of adjacent structural elements in the array to promote interlocking of adjacent structural elements in a relatively tightly meshed relationship for resisting shear stress in essentially all directions within the array.

2. The invention of claim 1 wherein the posts project radially from the hub, the length of each post extends longitudinally from the hub along the post, and the transverse cross-sectional configuration extends laterally across the post.

3. The invention of claim 2 wherein each post is tapered along the length thereof from a larger cross-sectional area adjacent the root of the post to a smaller cross-sectional area adjacent the tip of the post, each post being tapered substantially entirely along the length thereof.

4. The invention of claim 2 wherein the transverse cross-sectional configuration is an oval.

5. The invention of claim 2 wherein the length of each post extends from the center of the hub to the tip of the post and is within the range of about 80 to 400 microns.

6. The invention of claim 2 wherein the length of each post extends from the center of the hub to the tip of the post and is within the range of about 0.8 to 4.0 millimeters.

7. The invention of claim 2 wherein the length of each post extends from the center of the hub to the tip of the post and is up to about 4.0 millimeters.

8. The invention of claim 1 wherein the structural element is constructed of a biocompatible ceramic material.

9. The invention of claim 1 wherein the structural element is constructed of a biocompatible microporous ceramic material and a selected agent is carried within the microporous ceramic material for dispersion at the site of the array.

10. The invention of claim 1 wherein the structural element is constructed of a biocompatible material and a selected agent is carried in a coating on the biocompatible material for dispersion at the site of the array.

11. The invention of claim 1 wherein the structural element is constructed of a biocompatible material and a selected agent is carried in a diffused coating along the biocompatible microporous material for dispersion at the site of the array.

12. The invention of claim 1 wherein the relative dimensions of the hub and the posts are such that upon placement of the structural elements in the array the ratio of surface area to space volume of the array is within the range of surface-to-volume ratios encountered in human natural cancellous bone.

13. A structural element for use in an array of such structural elements interlocked with one another to augment or replace natural bone, the structural element comprising:
    a hub having a center; and
    four posts projecting radially from the hub and spaced apart from one another at equal angles in a caltrop configuration to establish inter-post spaces between adjacent posts, each post having a root at the hub, an opposite tip, a length extending longitudinally from the hub along the post, and a transverse cross-sectional configuration extending laterally across the post;
    the relative length, cross-sectional configuration, and location of adjacent posts in the structural element being such that upon placement of the structural elements in the array the inter-post spaces of one structural element will receive the posts of adjacent structural elements in the array to promote interlocking of adjacent structural elements in a relatively tightly meshed relationship for resisting shear stress in essentially all directions within the array.

14. An array of structural elements interlocked with one another to augment or replace natural bone, each structural element comprising:
    a hub having a center; and
    at least four posts projecting from the hub in directions relative to one another such that no more than two of the directions of any posts of the structural element lie in a common plane and the posts are spaced from one another to establish inter-post spaces between adjacent posts, each post having a root at the hub, an opposite tip, a length, and a transverse cross-sectional configuration;
    the relative length, cross-sectional configuration, and relative location of the posts in the structural element being such that the inter-post spaces of one structural element receive the posts of adjacent structural elements in the array to attain interlocking of adjacent structural elements in a relatively tightly meshed relationship for resisting shear stress in essentially all directions within the array.

15. The invention of claim 14 wherein the posts project radially from the hub, the length of each post extends longitudinally from the hub along the post, and the transverse cross-sectional configuration extends laterally across the post.

16. The invention of claim 15 wherein each post is tapered along the length thereof from a larger cross-sectional area adjacent the root of the post to a smaller cross-sectional area adjacent the tip of the post, each post being tapered substantially entirely along the length thereof.

17. The invention of claim 15 wherein the transverse cross-sectional configuration is an oval.

18. The invention of claim 15 wherein the length of each post extends between the center of the hub and the tip of the post and is within a range of about 80 to 400 microns.

19. The invention of claim 15 wherein the length of each post extends between the center of the hub and the tip of the post and is within a range of about 0.8 to 4.0 millimeters.

20. The invention of claim 15 wherein the length of each post extends between the center of the hub and the tip of the post and is up to about 4.0 millimeters.

21. The invention of claim 14 wherein the structural element is constructed of a biocompatible ceramic material.

22. The invention of claim 14 wherein the structural element is constructed of a biocompatible microporous ceramic material and a selected agent is carried within the microporous ceramic material for dispersion at the site of the array.

23. The invention of claim 14 wherein the structural element is constructed of a biocompatible material and a selected agent is carried in a coating on the biocompatible material for dispersion at the site of the array.

24. The invention of claim 14 wherein the structural element is constructed of a biocompatible material and a selected agent is carried in a diffused coating along the biocompatible microporous material for dispersion at the site of the array.

25. The invention of claim 14 wherein the array has a surface area and a space volume, and the relative dimensions of the hub and the posts are such that the ratio of surface area to space volume of the array is within the range of surface-to-volume ratios encountered in human natural cancellous bone.

26. An array of structural elements interlocked with one another to augment or replace natural bone, each structural element comprising:

a hub having a center; and four posts projecting from the hub and spaced apart from one another at equal angles in a caltrop configuration to establish inter-post spaces between adjacent posts, each post having a root at the hub, an opposite tip, a length extending longitudinally from the hub along the post, and a transverse cross-sectional configuration extending laterally across the post;

the relative length, cross-sectional configuration, and location of adjacent posts in each structural element being such that the inter-post spaces of one structural element receive the posts of adjacent structural elements in the array to attain interlocking of adjacent structural elements in a relatively tightly meshed relationship for resisting shear stress in essentially all directions within the array.

27. The method of repairing, augmenting or replacing natural bone by establishing an array of structural elements in a void in the natural bone, each structural element including:

a hub having a center; and at least four posts projecting from the hub in directions relative to one another such that no more than two of the directions of any posts of the structural element lie in a common plane and the posts are spaced from one another to establish inter-post spaces between adjacent posts, each post having a root at the hub, an opposite tip, a length, and a transverse cross-sectional configuration;

the relative length, cross-sectional configuration, and relative location of the posts in each structural element being such that upon establishing the array the inter-post spaces of one structural element receive the posts of adjacent structural elements in the array to attain interlocking of adjacent structural elements in a relatively tightly meshed relationship for resisting shear stress in essentially all directions within the array.

28. The invention of claim 27 wherein the void is a cavity between a prosthetic implant and the natural bone, and the array is established by placing the structural elements in the cavity.

29. The invention of claim 28 including mixing the structural elements with autologous bone to form a mixture, and subsequently filling the cavity with the mixture of structural elements and autologous bone.

30. The invention of claim 27 wherein the void is a defect in the natural bone, and the array is established by placing the structural elements in the defect.

31. The invention of claim 30 including mixing the structural elements with autologous blood to form a mixture, and subsequently filling the defect with the mixture of structural elements and autologous blood.

\* \* \* \* \*